United States Patent [19]

Rudolph et al.

[11] Patent Number: 5,015,784

[45] Date of Patent: May 14, 1991

[54] ISOMERIZATION OF BISPHENOLS

[75] Inventors: Udo Rudolph; Claus Wulff, both of Krefeld, Fed. Rep. of Germany

[73] Assignee: Bayer Aktiengesellschaft, Leverkusen, Fed. Rep. of Germany

[21] Appl. No.: 389,354

[22] Filed: Aug. 3, 1989

[30] Foreign Application Priority Data

Aug. 16, 1988 [DE] Fed. Rep. of Germany ....... 3827643

[51] Int. Cl.$^5$ .................... C07C 37/14; C07C 39/16
[52] U.S. Cl. .................... 568/722; 568/723; 568/783
[58] Field of Search .............. 568/722, 723, 86, 153

[56] References Cited

U.S. PATENT DOCUMENTS

| | | | |
|---|---|---|---|
| 4,156,790 | 5/1979 | Campbell | 568/783 |
| 4,822,923 | 4/1989 | Li | 568/722 |
| 4,825,010 | 4/1989 | Li | 568/722 |

FOREIGN PATENT DOCUMENTS

| | | | |
|---|---|---|---|
| 0098229 | 6/1982 | Japan | 568/722 |
| 0114540 | 7/1982 | Japan | 568/722 |
| 0122434 | 7/1984 | Japan | 568/722 |
| 1118335 | 6/1986 | Japan | 568/722 |
| 2029543 | 2/1987 | Japan | 568/722 |
| 2201833 | 9/1987 | Japan | 568/722 |
| 1066137 | 2/1967 | United Kingdom | 568/783 |
| 1474168 | 5/1977 | United Kingdom | 568/783 |

*Primary Examiner*—Werren B. Lone
*Attorney, Agent, or Firm*—Connolly and Hutz

[57] ABSTRACT

This invention relates to a process for the preparation of bisphenols and bisphenol mixtures by the isomerization of bisphenols on acid or alkaline catalysts in the presence of the corresponding phenols.

3 Claims, No Drawings

ISOMERIZATION OF BISPHENOLS

This invention relates to a process for the preparation of bisphenols and bisphenol mixtures by the isomerization of bisphenols on acid or alkaline catalysts in the presence of the corresponding phenols.

Bisphenols are important raw materials for chemical products such as epoxide resins and polycarbonates based e.g. on bisphenol A. The properties of the polycarbonate may be modified for certain applications by adding other polycarbonates to these polymers, e.g. polycarbonates based on other bisphenols, e.g. for the purpose of increasing the flame resIstance of polycarbonates based on tetrachloro or tetrabromobisphenol A. etc., for increasing the heat distortion temPerature of polycarbonates based on tetramethyl bisphenol, etc . . .

These processes are very complicated. They require not only a polycarbonate based on bisphenol A but in addition the preparation of a sufficient quantity of another bisphenol and of the corresponding polycarbonate. There are only a few bisphenols on the market apart from bisphenol A so that the preparation of other bisphenols generally requires development of a new process. Moreover, mixing of the polymers requires an additional step, e.g. of extrusion.

It has now been found that bisphenols isomerize in the presence of a certain phenol, e.g. 2,6-dimethyl phenol, in the presence of a suitable catalyst.

Bisphenol A and alkyl phenols, for example, may be converted into 3,5-dimethyl-4,4'-dihydroxydiphenyl-2,2-propane and/or 3,3',5,5'-tetramethyl-4,4-dihydroxydiphenyl-2,2-propane and/or 1,1,3,4,6-pentamethyl-3-(3,5-dimethyl-4-hydroxyphenyl)- indan-5-ol.

The present invention therefore relates to a process for the isomerization of bisphenols, characterized in that bisphenols are reacted with phenols in the presence of catalysts.

According to the invention, bisphenol A, for example, can readily be isomerized into the following bisphenols in the presence of 2,6-dimethyl phenol and in the presence of a suitable catalyst:

3,5-dimethyl-4,4'-dihydroxydiphenyl-2,2-propane (I)

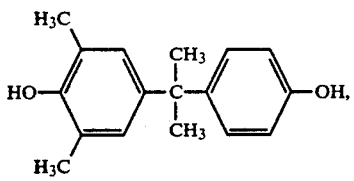

3,3',5,5'-tetramethyl-4,4'-dihydroxydiphenyl-2,2-propane (II)

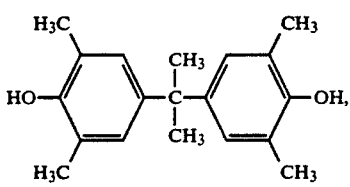

1,1,3,4,6-pentamethyl-3-(3,5-dimethyl-4-hydroxyphenyl)-indan-5-ol (III)

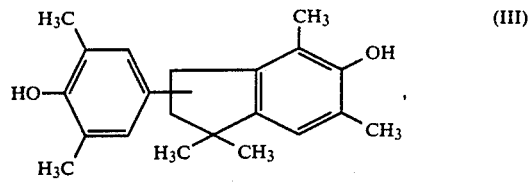

Bisphenol A, for example, will give rise to other bisphenols in the presence of suitable catalysts and in the presence of other phenols. Suitable other phenols have at least one unsubstituted position on the aromatic ring. The following are examples: mono- to tetra-$C_1$-$C_{12}$-alkyl-substituted phenols such as o-, m- and p-methyl phenol, o-, m-, and p-ethyl phenol, etc.; 2,6-dimethyl phenol etc.; mono or multi halogenated phenols (e.g. with Cl or Br) such as o-, m- and p-chlorophenol, o-, m- and p-bromophenol, 2,6-dichlorophenol, 2,6-dibormophenol, etc.; mono- or multi- $C_1$-$C_{10}$-alkoxy-substituted phenols and mono- or multi- $C_6$-$C_{24}$-aryl or $C_5$-$C_{30}$-cycloalkyl-substituted phenols, etc. Multinuclear phenols may also be used according to the invention.

Bisphenols corresponding to formula (IV)

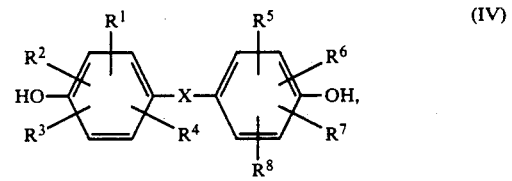

wherein $R^1$ to $R^8$ may be identical or different and denote. independently of one another, hydrogen or $C_1$ to $C_{12}$ alkyl and X denotes a $C_1$ to $C_{12}$ alkylidene or $C_3$ to $C_{12}$ cycloalkylidene group in the ortho or para position to the OH group may also be used according to the invention.

The following are examples of bisphenols corresponding to formula (IV): 2,2-bis-(4-hydroxyphenol)-propane (bisphenol A), 2,2-bis-(4-hydroxyphenyl)-butane, 2,2-bis-(4-hydroxyphenyl)-2-methylbutane and 1,1-bis-(4-hydroxyphenyl)-cyclohexane. Bisphenol A is preferred.

The phenols may be compounds corresponding to formula (V)

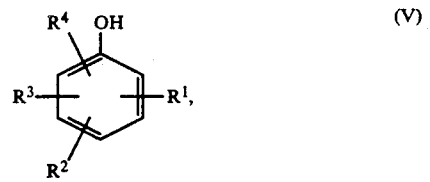

wherein $R^1$, $R^2$, $R^3$ and $R^4$ denote, independently of one another, hydrogen, $C_1$ to $C_{12}$ alkyl, halogen (e.g. Cl, Br), $C_6$ to $C_{24}$ aryl, $C_1$ to $C_{12}$ alkoxy or $C_5$ to $C_{30}$ cycloalkyl, $C_1$ $C_{12}$ alkyl being preferred.

The catalysts used according to the invention may be acids or bases, preferably acids for example protonic acids such as hydrohalic acids, e.g. hydrochloric acid; sulphuric acid, perchloric acid, benzene sulphonic acid, lewis acids such as borone trifluoride, acid ion exchange resins, etc . . . Acid ion exchange resins are preferred.

The catalysts may be used e.g. with the addition of sulphurcontaining compounds such as those commonly used e.g. for the preparation of bisphenol A from phenol and acetone. U.S. Pat. Nos. 2,468,982 and 2,623,908, for example, disclose the use of e.g. thioglycolic acid and 3-mercaptoproprionic acid; the addition of thiophenols is known from U.S. Pat. No. 2,359,242, the addition of alkyl mercaptans is known from U.S. Pat. No. 2,775,620 and the addition of hydrogen sulphide is known from Chemical Abstracts 58, 1403e. The ion exchange resins may be partly or completely neutralized with mercapto amines or thiazolines (e.g. U.S. Pat. No. 3,394,089).

Examples of suitable acid ion exchangers include the commercially available reaction products of styrene-divinyl benzene copolymers with conventional sulphonating agents such as sulphuric acid, chlorosulphonic acid, etc . . . They may be available e.g. in a spherical form, (particle sizes from 0.3 to 1.5 mm in diameter). They may have a normal or a monodisperse diameter distribution. Their total capacity of acid functions in a water-moist form with a water content of about 75 to 85% by weight ranges from 0.7 to 2.1 mval/ml of ion exchanger, preferably from 3.5 to 5 mval, based on 1 g of dry substance of ion exchanger.

The reaction according to the invention is carried out at the temperatures normally employed for the preparation of bisphenol. Temperatures from 20° to 150° C., especially from 40° to 80° C. have proved to be suitable. The reaction may be carried out at pressures below or above normal pressure, e.g. at $10^{-3}$ to $10^{-5}$ bar. Normal pressure is preferred.

The water moist ion exchangers may be dried before their use according to the invention by means of heat (20° to 150° C.), optionally under vacuum (up to $10^{-5}$ bar) or optionally by washing with hydrophilic organic liquids such as alcohols (e.g. methanol, ethanol or propanols) or phenols or by azeotropic distillation with organic liquids such as toluene, xylene, methylene chloride, etc . . .

The ion exchange resin is then rinsed with the phenol required for the preparation of the bisphenol and the bisphenol which is to be converted is dissolved in this medium at temperatures above the melting point of the phenol. The reaction mixture obtained after the reaction of bisphenol and phenol may be worked up by the usual methods such as distillation, crystallization, etc . . .

The process may be carried out continuously or batch wise.

The bisphenol or mixture of bisphenols prepared by this process may be used for known applications and is suitable in particular for the preparation of polycarbonates and of polymer alloys obtainable from the polycarbonates.

EXAMPLE 1

228 g of bisphenol A (1 mol), 1464 g of 2,6-dimethyl phenol (12 mol), about 250 g of ion exchange resin Lewatit (manufacturers Bayer AG) moist with dimethyl phenol and 0.68 g of β-mercaptopropionic acid are stirred together in a conventional laboratory apparatus at about 60° C. and the progress of conversion is monitored gas chromatographically. By the end of 6 hours, about 25% of 3,5-dimethyl-4,4'-dihydroxydiphenyl-2,2-propane, about 10% of 3,3'-5,5'-tetramethyl-4,4'-dihydroxydiphenyl-2,2-propane and about 5% of 1,1,3,4,6-pentamethyl-3-(3,5-dimethyl-4-hydroxyphenyl)-indan-5-ol have formed from the bisphenol A.

White crystals of the bisphenol mixture described above are obtained after removal of the ion exchanger by filtration and distillation of the phenol.

EXAMPLE 2

228 g of bisphenol A (1 mol), 1296 g of o-cresol (12 mol), about 250 g of o-cresol-moist ion exchange resin Lewatit SC 102 ® (manufacturer Bayer AG) and 0.68 g of β-mercaptopropionic acid are stirred together in a conventional laboratory apparatus at about 60° C. and the progress of conversion is monitored gas chromatographically. By the end of 5 hours, about 25% of the bisphenol A has been converted into 3-methyl-4,4'-dihydroxydiphenyl-2,2-propane, 20% has been converted into 3,3'-dimethyl-4,4'-dihydroxydiphenyl-2,2-propane and about 5% has been converted into indans. White crystals of the bisphenol mixture described above are obtained after the ion exchanger has been filtered off and the phenol distilled off.

What is claimed is:

1. In the process for isomerization of bisphenols in the presence of phenols and catalyst, the improvement comprises contacting a bisphenol of the formula

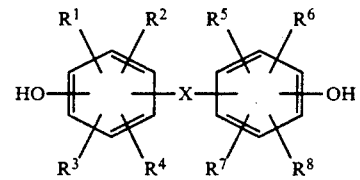

with a phenol of the formula

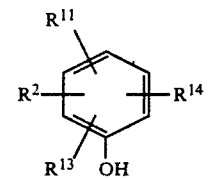

and a catalyst selected from the group consisting of protonic acids, Lewis acids and acid ion exchange resins,
wherein
$R^1$ to $R^8$ are the same or different and each is, independent of the others, hydrogen or alkyl having 1-12 carbon atoms,
X is alkylidene having 1-12 carbon atoms or cycloalkylidene having 3-12 carbon atoms, with X in the ortho or para position to the —OH,
$R^{11}$ to $R^{14}$ are the same or different and each is, independent of the others, alkyl having 1-12 carbon atoms, halogen, aryl having 6-24 carbon atoms, alkoxy having 1-12 carbons atoms or cycloalkyl having 5-30 carbon atoms.

2. The process according to claim 1 wherein the catalyst is an acid ion exchange resin, which is the reaction product of styrene/divinyl benzene copolymers with a sulfonating agent, having particle sizes of 0.3 to 1.5 mm in diameter and having a total capacity of acid functions in a water-moist form with a water content of about 75-85% by weight ranging from 0.7 to 2.1 m val/ml of ion exchanger based on one gram of dry exchanger.

3. Bisphenol mixtures obtained by the process according to claim 1.

* * * * *